US008571655B2

(12) United States Patent
Pastore et al.

(10) Patent No.: US 8,571,655 B2
(45) Date of Patent: *Oct. 29, 2013

(54) MULTI-SITE VENTRICULAR PACING THERAPY WITH PARASYMPATHETIC STIMULATION

(75) Inventors: Joseph M. Pastore, Concord, OH (US); Zoe Harris-Hajenga, St. Paul, MN (US); Julio C. Spinelli, Buenos Aires (AR)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/693,660

(22) Filed: Jan. 26, 2010

(65) Prior Publication Data

US 2010/0125307 A1    May 20, 2010

Related U.S. Application Data (63) Continuation of application No. 10/700,368, filed on Nov. 3, 2003, now Pat. No. 7,657,312.

(51) Int. Cl.
    *A61N 1/368* (2006.01)
(52) U.S. Cl.
    USPC ...................................... 607/14; 607/2; 607/9
(58) Field of Classification Search
    USPC .................................... 607/2, 9, 14
    See application file for complete search history.

(56) References Cited

U.S. PATENT DOCUMENTS

| | | | |
|---|---|---|---|
| 3,421,511 A | 1/1969 | Schwartz et al. | |
| 3,522,811 A | 8/1970 | Seymour et al. | |
| 3,557,796 A * | 1/1971 | Keller et al. | 607/9 |
| 3,650,277 A | 3/1972 | Sjostrand et al. | |
| 4,357,946 A | 11/1982 | Dutcher et al. | |
| 4,397,946 A | 8/1983 | Imada et al. | |
| 4,730,619 A | 3/1988 | Koning et al. | |
| 4,770,177 A | 9/1988 | Schroeppel | |
| 4,791,931 A | 12/1988 | Slate | |
| 4,936,304 A | 6/1990 | Kresh et al. | |
| 4,960,129 A | 10/1990 | dePaola et al. | |
| 5,024,222 A | 6/1991 | Thacker | |
| 5,052,388 A | 10/1991 | Sivula et al. | |
| 5,111,815 A | 5/1992 | Mower | |
| 5,190,035 A | 3/1993 | Salo et al. | |

(Continued)

FOREIGN PATENT DOCUMENTS

| | | |
|---|---|---|
| EP | 0547734 A2 | 6/1993 |
| EP | 1304135 A2 | 4/2003 |

(Continued)

OTHER PUBLICATIONS

"U.S. Appl. No. 10/700,368, Final Office Action mailed Oct. 15, 2008", 12 pgs.

(Continued)

*Primary Examiner* — Niketa Patel
*Assistant Examiner* — Christopher A Flory
(74) *Attorney, Agent, or Firm* — Schwegman Lundberg & Woessner, P.A.

(57) ABSTRACT

A method and device for delivering multi-site ventricular pacing therapy in conjunction with parasympathetic stimulation for reducing ventricular wall stress. Such reduction in ventricular wall stress is useful in reversing or preventing the ventricular remodeling which can occur in heart failure patients.

9 Claims, 2 Drawing Sheets

(56) References Cited

U.S. PATENT DOCUMENTS

| | | |
|---|---|---|
| 5,199,428 A | 4/1993 | Obel et al. |
| 5,203,326 A | 4/1993 | Collins |
| 5,243,980 A | 9/1993 | Mehra |
| 5,275,826 A | 1/1994 | Badylak et al. |
| 5,318,592 A | 6/1994 | Schaldach |
| 5,324,316 A | 6/1994 | Schulman et al. |
| 5,330,507 A | 7/1994 | Schwartz |
| 5,334,221 A | 8/1994 | Bardy |
| 5,356,425 A | 10/1994 | Bardy et al. |
| 5,374,282 A | 12/1994 | Nichols et al. |
| 5,403,351 A | 4/1995 | Saksena |
| 5,409,009 A | 4/1995 | Olson |
| 5,411,531 A | 5/1995 | Hill et al. |
| 5,437,285 A | 8/1995 | Verrier et al. |
| 5,507,784 A | 4/1996 | Hill et al. |
| 5,513,644 A | 5/1996 | McClure et al. |
| 5,522,854 A | 6/1996 | Ideker et al. |
| 5,540,730 A | 7/1996 | Terry, Jr. et al. |
| 5,562,711 A | 10/1996 | Yerich et al. |
| 5,578,061 A | 11/1996 | Stroetmann et al. |
| 5,651,378 A | 7/1997 | Matheny et al. |
| 5,658,318 A | 8/1997 | Stroetmann et al. |
| 5,662,689 A | 9/1997 | Elsberry et al. |
| 5,690,681 A | 11/1997 | Geddes et al. |
| 5,707,400 A | 1/1998 | Terry, Jr. et al. |
| 5,749,900 A | 5/1998 | Schroeppel et al. |
| 5,792,187 A | 8/1998 | Adams |
| 5,817,131 A | 10/1998 | Elsberry et al. |
| 5,902,324 A | 5/1999 | Thompson et al. |
| 5,913,876 A | 6/1999 | Taylor et al. |
| 5,916,239 A | 6/1999 | Geddes et al. |
| 6,006,122 A | 12/1999 | Smits |
| 6,006,134 A | 12/1999 | Hill et al. |
| 6,035,233 A | 3/2000 | Schroeppel et al. |
| 6,058,331 A | 5/2000 | King |
| 6,073,048 A | 6/2000 | Kieval et al. |
| 6,076,014 A | 6/2000 | Alt |
| 6,104,956 A | 8/2000 | Naritoku et al. |
| 6,115,628 A | 9/2000 | Stadler et al. |
| 6,119,043 A | 9/2000 | Hsu et al. |
| 6,134,470 A | 10/2000 | Hartlaub |
| 6,141,590 A | 10/2000 | Renirie et al. |
| 6,144,878 A | 11/2000 | Schroeppel et al. |
| 6,161,042 A | 12/2000 | Hartley et al. |
| 6,161,048 A | 12/2000 | Sluijter et al. |
| 6,164,284 A | 12/2000 | Schulman et al. |
| 6,169,918 B1 | 1/2001 | Haefner et al. |
| 6,178,349 B1 | 1/2001 | Kieval |
| 6,181,966 B1 | 1/2001 | Nigam |
| 6,208,902 B1 | 3/2001 | Boveja |
| 6,240,314 B1 | 5/2001 | Plicchi et al. |
| 6,240,316 B1 | 5/2001 | Richmond et al. |
| 6,266,564 B1 | 7/2001 | Hill et al. |
| 6,272,377 B1 | 8/2001 | Sweeney et al. |
| 6,285,907 B1 | 9/2001 | Kramer et al. |
| 6,292,695 B1 | 9/2001 | Webster, Jr. et al. |
| 6,292,703 B1 | 9/2001 | Meier et al. |
| 6,308,104 B1 | 10/2001 | Taylor et al. |
| 6,341,236 B1 | 1/2002 | Osorio et al. |
| 6,349,233 B1 | 2/2002 | Adams |
| 6,371,922 B1 | 4/2002 | Baumann et al. |
| 6,381,499 B1 | 4/2002 | Taylor et al. |
| 6,400,982 B2 | 6/2002 | Sweeney et al. |
| 6,405,079 B1 | 6/2002 | Ansarinia |
| 6,411,845 B1 | 6/2002 | Mower |
| 6,421,557 B1 | 7/2002 | Meyer |
| 6,438,423 B1 | 8/2002 | Rezai et al. |
| 6,442,424 B1 | 8/2002 | Ben-Haim et al. |
| 6,447,443 B1 | 9/2002 | Keogh et al. |
| 6,449,507 B1 | 9/2002 | Hill et al. |
| 6,473,644 B1 | 10/2002 | Terry, Jr. et al. |
| 6,477,418 B2 | 11/2002 | Plicchi et al. |
| 6,487,442 B1 | 11/2002 | Wood |
| 6,487,446 B1 | 11/2002 | Hill et al. |
| 6,487,450 B1 | 11/2002 | Chen et al. |
| 6,493,585 B2 | 12/2002 | Plicchi et al. |
| 6,511,500 B1 | 1/2003 | Rahme |
| 6,522,926 B1 | 2/2003 | Kieval et al. |
| 6,532,388 B1 | 3/2003 | Hill et al. |
| 6,542,774 B2 | 4/2003 | Hill et al. |
| 6,544,270 B1 | 4/2003 | Zhang |
| 6,564,096 B2 | 5/2003 | Mest |
| 6,571,121 B2 | 5/2003 | Schroeppel et al. |
| 6,571,122 B2 | 5/2003 | Schroeppel et al. |
| 6,574,512 B1 | 6/2003 | Zhang et al. |
| 6,584,362 B1 | 6/2003 | Scheiner et al. |
| 6,600,954 B2 | 7/2003 | Cohen et al. |
| 6,610,713 B2 | 8/2003 | Tracey |
| 6,611,713 B2 | 8/2003 | Schauerte |
| 6,622,041 B2 | 9/2003 | Terry, Jr. et al. |
| 6,628,987 B1 | 9/2003 | Hill et al. |
| 6,662,052 B1 | 12/2003 | Sarwal et al. |
| 6,668,191 B1 | 12/2003 | Boveja |
| 6,684,105 B2 | 1/2004 | Cohen et al. |
| 6,690,971 B2 | 2/2004 | Schauerte et al. |
| 6,718,203 B2 | 4/2004 | Weiner et al. |
| 6,718,207 B2 | 4/2004 | Connelly |
| 6,718,208 B2 | 4/2004 | Hill et al. |
| 6,735,471 B2 | 5/2004 | Hill et al. |
| 6,763,268 B2 | 7/2004 | MacDonald et al. |
| 6,778,854 B2 | 8/2004 | Puskas |
| 6,788,970 B1 | 9/2004 | Park et al. |
| 6,799,069 B2 | 9/2004 | Weiner et al. |
| 6,804,561 B2 | 10/2004 | Stover |
| RE38,654 E | 11/2004 | Hill et al. |
| 6,839,592 B2 | 1/2005 | Grandjean |
| 6,845,267 B2 | 1/2005 | Harrison et al. |
| RE38,705 E | 2/2005 | Hill et al. |
| 6,882,886 B1 | 4/2005 | Witte et al. |
| 6,885,888 B2 | 4/2005 | Rezai |
| 6,904,318 B2 | 6/2005 | Hill et al. |
| 6,912,419 B2 | 6/2005 | Hill et al. |
| 6,922,585 B2 | 7/2005 | Zhou et al. |
| 6,928,320 B2 | 8/2005 | King |
| 6,928,324 B2 | 8/2005 | Park et al. |
| 6,928,326 B1 | 8/2005 | Levine |
| 6,934,583 B2 | 8/2005 | Weinberg et al. |
| 6,937,896 B1 | 8/2005 | Kroll |
| 6,942,622 B1 | 9/2005 | Turcott |
| 6,985,774 B2 | 1/2006 | Kieval et al. |
| 6,988,007 B1 | 1/2006 | Morgan et al. |
| 7,025,730 B2 | 4/2006 | Cho et al. |
| 7,058,450 B2 | 6/2006 | Struble et al. |
| 7,069,070 B2 | 6/2006 | Carlson et al. |
| 7,072,720 B2 | 7/2006 | Puskas |
| 7,092,755 B2 | 8/2006 | Florio |
| 7,123,959 B2 | 10/2006 | Cates |
| 7,123,967 B2 | 10/2006 | Weinberg |
| 7,139,607 B1 | 11/2006 | Shelchuk |
| 7,155,284 B1 | 12/2006 | Whitehurst et al. |
| 7,158,832 B2 | 1/2007 | Kieval et al. |
| 7,191,015 B2 | 3/2007 | Lamson et al. |
| 7,194,313 B2 | 3/2007 | Libbus |
| 7,225,017 B1 | 5/2007 | Shelchuk |
| 7,245,967 B1 | 7/2007 | Shelchuk |
| 7,260,431 B2 | 8/2007 | Libbus et al. |
| 7,277,761 B2 | 10/2007 | Shelchuk |
| 7,294,334 B1 | 11/2007 | Michal et al. |
| 7,321,793 B2 | 1/2008 | Ben Ezra et al. |
| 7,333,854 B1 | 2/2008 | Brewer et al. |
| 7,340,299 B2 | 3/2008 | Puskas |
| 7,403,819 B1 | 7/2008 | Shelchuk et al. |
| 7,460,906 B2 | 12/2008 | Libbus |
| 7,486,991 B2 | 2/2009 | Libbus et al. |
| 7,509,166 B2 | 3/2009 | Libbus |
| 7,587,238 B2 | 9/2009 | Moffitt et al. |
| 7,643,875 B2 | 1/2010 | Hiel, Jr. et al. |
| 7,647,114 B2 | 1/2010 | Libbus |
| 7,657,312 B2 | 2/2010 | Pastore et al. |
| 7,706,884 B2 | 4/2010 | Libbus |
| 2001/0020136 A1 | 9/2001 | Sweeney et al. |
| 2002/0004670 A1 | 1/2002 | Florio et al. |
| 2002/0010493 A1 | 1/2002 | Poezevara et al. |
| 2002/0016344 A1 | 2/2002 | Tracey |
| 2002/0016550 A1 | 2/2002 | Sweeney et al. |

(56) References Cited

U.S. PATENT DOCUMENTS

| | | |
|---|---|---|
| 2002/0026221 A1 | 2/2002 | Hill et al. |
| 2002/0026222 A1 | 2/2002 | Schauerte et al. |
| 2002/0026228 A1 | 2/2002 | Schauerte |
| 2002/0032468 A1 | 3/2002 | Hill et al. |
| 2002/0035378 A1 | 3/2002 | Bardy et al. |
| 2002/0042637 A1 | 4/2002 | Stover |
| 2002/0058877 A1 | 5/2002 | Baumann et al. |
| 2002/0068875 A1 | 6/2002 | Schroeppel et al. |
| 2002/0072776 A1 | 6/2002 | Osorio et al. |
| 2002/0077670 A1 | 6/2002 | Archer et al. |
| 2002/0082661 A1 | 6/2002 | Plicchi et al. |
| 2002/0091415 A1 | 7/2002 | Lovett et al. |
| 2002/0095139 A1 | 7/2002 | Keogh et al. |
| 2002/0107553 A1 | 8/2002 | Hill et al. |
| 2002/0107557 A1 | 8/2002 | Edell et al. |
| 2002/0116030 A1 | 8/2002 | Rezai |
| 2002/0120304 A1 | 8/2002 | Mest |
| 2002/0123769 A1 | 9/2002 | Panken et al. |
| 2002/0138109 A1 | 9/2002 | Keogh et al. |
| 2002/0143369 A1 | 10/2002 | Hill et al. |
| 2002/0161410 A1 | 10/2002 | Kramer et al. |
| 2002/0165586 A1 | 11/2002 | Hill et al. |
| 2002/0183237 A1 | 12/2002 | Puskas |
| 2002/0183793 A1 | 12/2002 | Struble et al. |
| 2002/0188325 A1 | 12/2002 | Hill et al. |
| 2002/0188326 A1 | 12/2002 | Zheng et al. |
| 2002/0193843 A1 | 12/2002 | Hill et al. |
| 2002/0198570 A1 | 12/2002 | Puskas |
| 2002/0198571 A1 | 12/2002 | Puskas |
| 2003/0003052 A1 | 1/2003 | Hampton |
| 2003/0004549 A1 | 1/2003 | Hill et al. |
| 2003/0018368 A1 | 1/2003 | Ansarinia |
| 2003/0023279 A1 | 1/2003 | Spinelli et al. |
| 2003/0036773 A1 | 2/2003 | Whitehurst et al. |
| 2003/0040774 A1 | 2/2003 | Terry et al. |
| 2003/0045909 A1 | 3/2003 | Gross et al. |
| 2003/0045914 A1 | 3/2003 | Cohen et al. |
| 2003/0060848 A1 | 3/2003 | Keival et al. |
| 2003/0060857 A1 | 3/2003 | Perrson et al. |
| 2003/0060858 A1 | 3/2003 | Kieval et al. |
| 2003/0074039 A1 | 4/2003 | Puskas |
| 2003/0078623 A1 | 4/2003 | Weinberg et al. |
| 2003/0078629 A1 | 4/2003 | Chen |
| 2003/0100924 A1 | 5/2003 | Foreman et al. |
| 2003/0105493 A1 | 6/2003 | Salo |
| 2003/0114905 A1 | 6/2003 | Kuzma |
| 2003/0149450 A1 | 8/2003 | Mayberg |
| 2003/0158584 A1 | 8/2003 | Cates et al. |
| 2003/0176818 A1 | 9/2003 | Schuler et al. |
| 2003/0181951 A1 | 9/2003 | Cates |
| 2003/0191403 A1 | 10/2003 | Zhou et al. |
| 2003/0191404 A1 | 10/2003 | Klein |
| 2003/0195578 A1 | 10/2003 | Perron et al. |
| 2003/0199958 A1 | 10/2003 | Zhang et al. |
| 2003/0212440 A1 | 11/2003 | Boveja |
| 2003/0216790 A1 | 11/2003 | Hill et al. |
| 2003/0216792 A1 | 11/2003 | Levin et al. |
| 2003/0229380 A1 | 12/2003 | Adams et al. |
| 2003/0236558 A1 | 12/2003 | Whitehurst et al. |
| 2004/0010303 A1 | 1/2004 | Bolea et al. |
| 2004/0015204 A1 | 1/2004 | Whitehurst et al. |
| 2004/0015205 A1 | 1/2004 | Whitehurst et al. |
| 2004/0019364 A1 | 1/2004 | Kieval et al. |
| 2004/0024422 A1 | 2/2004 | Hill et al. |
| 2004/0030362 A1 | 2/2004 | Hill et al. |
| 2004/0038857 A1 | 2/2004 | Tracey |
| 2004/0048795 A1 | 3/2004 | Ivanova et al. |
| 2004/0049120 A1 | 3/2004 | Cao et al. |
| 2004/0049235 A1 | 3/2004 | Deno et al. |
| 2004/0054381 A1 | 3/2004 | Pastore et al. |
| 2004/0059383 A1 | 3/2004 | Puskas |
| 2004/0068299 A1 | 4/2004 | Laske et al. |
| 2004/0088009 A1 | 5/2004 | Degroot |
| 2004/0088015 A1 | 5/2004 | Casavant et al. |
| 2004/0098057 A1 | 5/2004 | Pastore |
| 2004/0116970 A1 | 6/2004 | Girouard et al. |
| 2004/0122496 A1 | 6/2004 | Zhang et al. |
| 2004/0122497 A1 | 6/2004 | Zhang et al. |
| 2004/0122498 A1 | 6/2004 | Zhang et al. |
| 2004/0127942 A1 | 7/2004 | Yomtov et al. |
| 2004/0127947 A1 | 7/2004 | Kim et al. |
| 2004/0133248 A1 | 7/2004 | Frei et al. |
| 2004/0138721 A1 | 7/2004 | Osorio et al. |
| 2004/0162594 A1 | 8/2004 | King |
| 2004/0172074 A1 | 9/2004 | Yoshihito |
| 2004/0172075 A1 | 9/2004 | Shafer et al. |
| 2004/0193231 A1 | 9/2004 | David et al. |
| 2004/0199209 A1 | 10/2004 | Hill et al. |
| 2004/0199210 A1 | 10/2004 | Shelchuk |
| 2004/0220621 A1 | 11/2004 | Zhou et al. |
| 2004/0249416 A1 | 12/2004 | Yun et al. |
| 2004/0254612 A1 | 12/2004 | Ezra et al. |
| 2005/0059897 A1 | 3/2005 | Snell et al. |
| 2005/0065554 A1 | 3/2005 | KenKnight et al. |
| 2005/0065555 A1 | 3/2005 | Er |
| 2005/0065562 A1 | 3/2005 | Rezai |
| 2005/0131467 A1 | 6/2005 | Boveja |
| 2005/0143779 A1 | 6/2005 | Libbus |
| 2005/0143785 A1 | 6/2005 | Libbus |
| 2005/0149126 A1 | 7/2005 | Libbus |
| 2005/0149127 A1 | 7/2005 | Libbus |
| 2005/0149129 A1 | 7/2005 | Libbus et al. |
| 2005/0149130 A1 | 7/2005 | Libbus |
| 2005/0149131 A1 | 7/2005 | Libbus et al. |
| 2005/0149132 A1 | 7/2005 | Libbus |
| 2005/0149133 A1 | 7/2005 | Libbus et al. |
| 2005/0149143 A1 | 7/2005 | Libbus et al. |
| 2005/0149156 A1 | 7/2005 | Libbus et al. |
| 2005/0222632 A1 | 10/2005 | Obino |
| 2005/0251216 A1 | 11/2005 | Hill et al. |
| 2006/0074453 A1 | 4/2006 | Kieval et al. |
| 2006/0089678 A1 | 4/2006 | Shalev |
| 2006/0095080 A1 | 5/2006 | Libbus et al. |
| 2006/0106429 A1 | 5/2006 | Libbus et al. |
| 2006/0116737 A1 | 6/2006 | Libbus |
| 2006/0134071 A1 | 6/2006 | Ross et al. |
| 2006/0134079 A1 | 6/2006 | Sih et al. |
| 2006/0136027 A1 | 6/2006 | Westlund et al. |
| 2006/0136028 A1 | 6/2006 | Ross et al. |
| 2006/0253156 A1 | 11/2006 | Pastore et al. |
| 2006/0271115 A1 | 11/2006 | Ben-Ezra et al. |
| 2007/0021790 A1 | 1/2007 | Kieval et al. |
| 2007/0021792 A1 | 1/2007 | Kieval et al. |
| 2007/0021796 A1 | 1/2007 | Kieval et al. |
| 2007/0021797 A1 | 1/2007 | Kieval et al. |
| 2007/0021798 A1 | 1/2007 | Kieval et al. |
| 2007/0021799 A1 | 1/2007 | Kieval et al. |
| 2007/0034261 A1 | 2/2007 | Eichler |
| 2007/0038259 A1 | 2/2007 | Kieval et al. |
| 2007/0038260 A1 | 2/2007 | Kieval et al. |
| 2007/0038261 A1 | 2/2007 | Kieval et al. |
| 2007/0060972 A1 | 3/2007 | Kieval et al. |
| 2007/0067008 A1 | 3/2007 | Scheiner et al. |
| 2007/0068260 A1 | 3/2007 | Hong et al. |
| 2007/0142864 A1 | 6/2007 | Libbus et al. |
| 2007/0142871 A1 | 6/2007 | Libbus et al. |
| 2007/0167984 A1 | 7/2007 | Kieval et al. |
| 2007/0191904 A1 | 8/2007 | Libbus et al. |
| 2008/0015648 A1 | 1/2008 | Libbus et al. |
| 2008/0015657 A1 | 1/2008 | Haefner |
| 2008/0021507 A1 | 1/2008 | Libbus et al. |
| 2008/0125843 A1 | 5/2008 | Ben-David et al. |
| 2010/0121399 A1 | 5/2010 | McCabe et al. |
| 2011/0295333 A1 | 12/2011 | Libbus |

FOREIGN PATENT DOCUMENTS

| | | |
|---|---|---|
| EP | 1486232 A2 | 12/2004 |
| EP | 1541193 A1 | 6/2005 |
| WO | WO-92/16257 A1 | 10/1992 |
| WO | WO-97/13550 A1 | 4/1997 |
| WO | WO-97/40885 A1 | 11/1997 |
| WO | WO-99/65561 A1 | 12/1999 |
| WO | WO-01/24876 A1 | 4/2001 |

(56) References Cited

FOREIGN PATENT DOCUMENTS

| WO | WO-01/76689 A2 | 10/2001 |
|---|---|---|
| WO | WO-02/26314 A1 | 4/2002 |
| WO | WO-02/26318 A1 | 4/2002 |
| WO | WO-0226320 A1 | 4/2002 |
| WO | WO-02/34327 A2 | 5/2002 |
| WO | WO-02/085448 A2 | 10/2002 |
| WO | WO-02/087694 A1 | 11/2002 |
| WO | WO-03/011388 A2 | 2/2003 |
| WO | WO-03/020364 A2 | 3/2003 |
| WO | WO-03/026741 A1 | 4/2003 |
| WO | WO-03/041559 A2 | 5/2003 |
| WO | WO-03/076008 A1 | 9/2003 |
| WO | WO-03/082080 A2 | 10/2003 |
| WO | WO-03/099373 A2 | 12/2003 |
| WO | WO-03/099377 A1 | 12/2003 |
| WO | WO-2004/012814 A1 | 2/2004 |
| WO | WO-2004/033036 A2 | 4/2004 |
| WO | WO-2005/113066 A1 | 12/2005 |
| WO | WO-2006121929 A1 | 11/2006 |
| WO | WO-2007/078410 A1 | 7/2007 |
| WO | WO-2011146393 A2 | 11/2011 |

OTHER PUBLICATIONS

"U.S. Appl. No. 10/700,368, Final Office Action mailed Oct. 31, 2007", 12 pgs.
"U.S. Appl. No. 10/700,368, Non Final Office Action mailed May 3, 2007", 11 pgs.
"U.S. Appl. No. 10/700,368, Non Final Office Action mailed Jul. 12, 2006", 19 pgs.
"U.S. Appl. No. 10/700,368, Non-Final Office Action mailed Feb. 25, 2009", 13 pgs.
"U.S. Appl. No. 10/700,368, Non-Final Office Action mailed Mar. 14, 2008", 13 pgs.
"U.S. Appl. No. 10/700,368, Notice of Allowance mailed Sep. 15, 2009", 7 pgs.
"U.S. Appl. No. 10/700,368, Response filed Jan. 15, 2009 to Final Office Action mailed Oct. 15, 2008", 8 pgs.
"U.S. Appl. No. 10/700,368, Response filed Jan. 31, 2008 to Final Office Action mailed Oct. 31, 2007", 8 pgs.
"U.S. Appl. No. 10/700,368, Response filed Jun. 16, 2008 to Non-Final Office Action mailed Mar. 14, 2008", 8 pgs.
"U.S. Appl. No. 10/700,368, Response filed Jul. 20, 2009 to Non Final Office Action mailed Feb. 25, 2009", 11 pgs.
"U.S. Appl. No. 10/700,368, Response filed Sep. 4, 2007 to Non-Final Office Action mailed May 3, 2007", 8 pgs.
"U.S. Appl. No. 10/700,368, Response filed Nov. 13, 2006 to Non Final Office Action mailed Jul. 12, 2006", 7 pgs.
European Application Serial No. 04800666.2, Communication dated Sep. 20, 2006, 3 pgs.
European Application Serial No. 04800666.2, Response filed Mar. 15, 2007 to Communication dated Sep. 20, 2006, 10 pgs.
"International Search Report for corresponding PCT Application No. PCT/US2004/036606", (Mar. 10, 2005), 4 pgs.
"Written Opinion for corresponding PCT Application No. PCT/US2004/036606", (Mar. 10, 2005), 5 pgs.
"Japanese Application Serial No. 2006-538456, Office Action mailed Apr. 6, 2010", (w/ English Translation), 4 pgs.
Abraham, W T, "Cardiac Resynchronization in Chronic Heart Failure", *New England Journal of Medicine*, 346(24), (Jul. 13, 2002), 1845-1853.
Andersen, H, et al., "Long-term follow-up of patients from a randomised trial of atrial versus ventricular pacing for sick-sinus syndrome", *Lancet*, 350(9086), (Oct. 25, 1997), 1210-1216.
Benchimol, A, et al., "Cardiac hemodynamics during stimulation of the right atrium, right ventricle, and left ventricle in normal and abnormal hearts", *Circulation*, 33(6), (Jun. 1966), 933-44.
Bevan, J A, et al., "Postganglionic sympathetic delay in vascular smooth muscle", *Journal of Pharmacology & Experimental Therapeutics*, 152(2), (May 1996), 221-30.

Bevan, J A, et al., "Sympathetic nerve-free vascular muscle", *Journal of Pharmacology & Experimental Therapeutics*, 157(1), (Jul. 1967), 117-24.
Bilgutay, A M, et al., "A new concept in the treatment of hypertension utilizing an implantable electronic device: "Baropacer"", *Trans Am Soc Artif Intern Organs.*, 10, (1964), 387-395.
Bilgutay, A M, et al., "Vagal tuning for the control of supraventricular arrhythmias", *Surgical Forum*, 16, (1965), 151-153.
Bilgutay, A. M, et al., "Vagal tuning, A new concept in the treatment of supraventricular arrhythmias, angina pectoris, and heart failure", *Journal of Thoracic and Cardiovascular Surgery*, 56(1), (Jul. 1968), 71-82.
Borst, C, et al., "Optimal frequency of carotid sinus nerve stimulation in treatment of angina pectoris", *Cardiovascular Research*, 8(5), (Sep. 1974), 674-80.
Braunwald, E, et al., "Carotid sinus nerve stimulation in the treatment of angina pectoris and supraventricular tachycardia", *California Medicine*, 112(3), (Mar. 1970), 41-50.
Braunwald, E, et al., "Relief of angina pectoris by electrical stimulation of the carotid-sinus nerves", *New England Journal of Medicine*, 277(24), (Dec. 14, 1967), 1278-83.
Chapleau, M W, "Neuro-cardiovascular regulation: from molecules to man. Introduction.", *Annals of the New York Academy of Sciences*, 940, (Jun. 2001), xiii-xxii.
Chapleau, M W, et al., "Pulsatile activation of baroreceptors causes central facilitation of baroreflex", *American Journal of Physiology*, 256(6 Pt 2), (Jun. 1989), H1735-41.
Coleridge, J C, et al., "Relationship between pulmonary arterial pressure and impulse activity in pulmonary arterial baroreceptor fibres", *Journal of Physiology*, 158, (Sep. 1961), 197-205.
Coleridge, J C, et al., "The distribution, connexions and histology of baroreceptors in the pulmonary artery, with some observations on the sensory innervation of the ductus arteriosus", *Journal of Physiology*, 156, (May 1961), 591-602.
Cooper, Terry B, et al., "Neural effects on sinus rate and atrioventricular conduction produced by electrical stimulation from a transvenous electrode catheter in the canine right pulmonary artery", *Circulation Research*, vol. 46, No. 1, (Jan. 1980), 48-57.
Courtice, G P, et al., "Effect of frequency and impulse pattern on the non-cholinergic cardiac response to vagal stimulation in the toad, Bufo marinus", *Journal of the Autonomic Nervous System*, 48(3), (Aug. 1994), 267-272.
Dart, Jr., C H, et al., "Carotid sinus nerve stimulation treatment of angina refractory to other surgical procedures", *Annals of Thoracic Surgery*, 11(4), (Apr. 1971), 348-359.
De Landsheere, D, et al., "Effect of spinal cord stimulation on regional myocardial perfusion assessed by positron emission tomography", *American Journal of Cardiology*, 69(14), (May 1, 1992), 1143-11149.
Dickerson, L W, "Parasympathetic neurons in the cranial medial ventricular fat pad on the dog heart selectively decrease ventricular contractility", *Journal of the Autonomic Nervous System*, 70(1-2), (May 28, 1998), 129-41.
Dunning, A. J., "Electrostimulation of the Carotid Sinus Nerve in Angina Pectoris", *University Department of Medicine*, Binnengasthuis, Amsterdam; Printed by Royal VanGorcum, Assen, Netherlands, (1971), 1-92.
Epstein, S. E., et al., "Treatment of angina pectoris by electrical stimulation of the carotid-sinus nerves", *New England Journal of Medicine*, 280(18), (May 1, 1969), 971-978.
Farrehi, C., "Stimulation of the carotid sinus nerve in treatment of angina pectoris", *American Heart Journal*, 80(6), (Dec. 1970), 759-765.
Feliciano, L., et al., "Vagal nerve stimulation releases vasoactive intestinal peptide which significantly increases coronary artery blood flow", *Cardiovascular Research*, 40(1), (Oct. 1998), 45-55.
Fromer, M., et al., "Ultrarapid subthreshold stimulation for termination of atrioventricular node reentrant tachycardia", *Journal of the American College of Cardiology*, 20(4), (Oct. 1992), 879-883.
Gatti, P. J., et al., "Vagal control of left ventricular contractility is selectively mediated by a cranioventricular intracardiac ganglion in the cat", *J Auton Nerv Syst.*, 66(3), (Oct. 13, 1997), 138-144.

(56) References Cited

OTHER PUBLICATIONS

Grassi, G., et al., "Baroreflex and non-baroreflex modulation of vagal cardiac control after myocardial infarction", *Am J Cardiol.*, 84(5), (Sep. 1, 1999), 525-9.

Griffith, L. S. C., et al., "Electrical Stimulation of the Carotid Sinus Nerve in Normotensive and Renal Hypertensive Dogs", *Circulation*, 28, (Jul.-Dec. 1963), p. 730.

Henning, R. J,, et al., "Effects of autonomic nerve stimulation, asynchrony, and load on dP/dtmax and on dP/dtmin", *American Journal of Physiology*, 260(4 Pt 2), (Apr. 1991), H1290-H1298.

Henning, R. J,, et al., "Vagal nerve stimulation increases right ventricular contraction and relaxation and heart rate", *Cardiovascular Research*, 32(5), (Nov. 1996), 846-853.

Henning, R. J., et al., "Vagal stimulation attenuates sympathetic enhancement of left ventricular function", *American Journal of Physiology*, 258(5 Pt 2), (May 1990), H1470-H1475.

Holder, L K, "Treatment of refractory partial seizures: preliminary results of a controlled study", *Pacing & Clinical Electrophysiology*, 15(10 Pt 2), (Oct. 1992), 1557-1571.

Hood Jr., W B, et al., "Asynchronous contraction due to late systolic bulging at left ventricular pacing sites", *American Journal of Physiology*, 217(1), (Jul. 1969), 215-221.

Ishise, H, et al., "Time course of sympathovagal imbalance and left ventricular dysfunction in conscious dogs with heart failure", *Journal of Applied Physiology*, 84(4), (Apr. 1998), 1234-1241.

Jessurun, G A, et al., "Coronary blood flow dynamics during transcutaneous electrical nerve stimulation for stable angina pectoris associated with severe narrowing of one major coronary artery", *American Journal of Cardiology*, 82(8), erratum appears in Am J Cardiol Feb. 15, 1999;83(4):642, (Oct. 15, 1998), 921-926.

Kandel, Eric R, et al., "Part VII: Arousal, Emotion, and Behavioral Homeostasis", *In: Principles of Neural Science*, New York : McGraw-Hill, Health Professions Division, (2000), 966-969.

Karpawich, P P, et al., "Altered cardiac histology following apical right ventricular pacing in patients with congenital atrioventricular block", *Pacing Clin Electrophysiol.*, 22(9), (Sep. 1999), 1372-1377.

Kendrick, J E, "A comparison of the cardiovascular responses to stimulation of the aortic and carotid sinus nerves of the dog", *Proceedings of the Society for Experimental Biology & Medicine*, 144(2), (Nov. 1973), 404-411.

Leclercq, C, et al., "Hemodynamic importance of preserving the normal sequence of ventricular activation in permanent cardiac pacing", *Am Heart J.*, 129(6), (Jun. 1995), 1133-1141.

Mannheimer, C, et al., "Epidural spinal electrical stimulation in severe angina pectoris", *British Heart Journal*, 59(1), (Jan. 1988), 56-61.

Mannheimer, C, et al., "Transcutaneous electrical nerve stimulation (TENS) in angina pectoris", *Pain*, 26(3), (Sep. 1986), 291-300.

Mannheimer, C, et al., "Transcutaneous electrical nerve stimulation in severe angina pectoris", *European Heart Journal*, 3(4), (Aug. 1982), 297-302.

Mazgalev, T N, et al., "Autonomic modification of the atrioventricular node during atrial fibrillation: role in the slowing of ventricular rate", *Circulation*, 99(21), (Jun. 1, 1999), 2806-2814.

Millar-Craig, M W, et al., "Circadian variation of blood-pressure", *Lancet*, 1(8068), (Apr. 15, 1978), 795-7.

Minisi, A J, et al., "Regional left ventricular deafferentation increases baroreflex sensitivity following myocardial infarction", *Cardiovasc Res.*, 58(1), (Apr. 1, 2003), 136-141.

Murphy, D F, et al., "Intractable angina pectoris: management with dorsal column stimulation", *Medical Journal of Australia*, 146(5), (Mar. 2, 1987), 260.

Neistadt, A, et al., "Effects of electrical stimulation of the carotid sinus nerve in reversal of experimentally induced hypertension", *Surgery*, 61(6), (Jun. 1967), 923-931.

Nolan, J., et al., "Prospective Study of Heart Rate Variability and Mortality in Chronic Heart Failure: Results of the United Kingdom Heart Failure Evaluation and Assessment of Risk Trial (UK-Heart).", *Circulation*, 98(15), (1998), 1510-1516.

Peters, T K, et al., "Temporal and spatial summation caused by aortic nerve stimulation in rabbits. Effects of stimulation frequencies and amplitudes", *Journal of the Autonomic Nervous System*, 27(3), (Aug. 1989), 193-205.

Peters, T K, et al., "The principle of electrical carotid sinus nerve stimulation: a nerve pacemaker system for angina pectoris and hypertension therapy", *Annals of Biomedical Engineering*, 8(4-6), (1980), 445-458.

Philbin, D M, et al., "Inappropriate shocks delivered by an ICD as a result of sensed potentials from a transcutaneous electronic nerve stimulation unit", *Pacing & Clinical Electrophysiology*, 21(10), (Oct. 1998), 2010-2011.

Prakash, P, et al., "Asymmetrical distribution of aortic nerve fibers in the pig", *Anat Rec.*, 158(1), (May 1967), 51-57.

Rosenqvist, M, et al., "The effect of ventricular activation sequence on cardiac performance during pacing", *Pacing and Electrophysiology*, 19(9), (1996), 1279-1286.

Rushmer, Robert F, "Chapter 5—Systemic Arterial Pressure", *In: Cardiovascular dynamics*, Philadelphia : Saunders, (1976), 176-216.

Schauerte, P, et al., "Catheter stimulation of cardiac parasympathetic nerves in humans: a novel approach to the cardiac autonomic nervous system", *Circulation*, 104(20), (Nov. 13, 2001), 2430-2435.

Schauerte, P, et al., "Ventricular rate control during atrial fibrillation by cardiac parasympathetic nerve stimulation: a transvenous approach", *J Am Coll Cardiol.*, 34(7), (Dec. 1999), 2043-2050.

Schauerte, P. N, et al., "Transvenous parasympathetic cardiac nerve stimulation: an approach for stable sinus rate control", *Journal of Cardiovascular Electrophysiology*, 10(11), (Nov. 1999), 1517-1524.

Schauerte, P., et al., "Transvenous Parasympathetic Nerve Stimulation in the Inferior Vena Cava and Atrioventricular Conduction", *Journal of Cardiovascular Electrophysiology*, 11(1), (Jan. 2000), 64-69.

Scheiner, Avram, "Stimulation Lead for Stimulating the Baroreceptors in the Pulmonary Artery", U.S. Appl. No. 10/746,852, filed Dec. 24, 2003, 25 pgs.

Scherlag, M A., et al., "Endovascular Neural Stimulation Via a Novel Basket Electrode Catheter: Comparison of Electrode Configurations", *Journal of Interventional Cardiac Electrophysiology*, 4(1), (Apr. 2000), 219-224.

Schmidt, E M, "Blood pressure response to aortic nerve stimulation in swine", *American Journal of Physiology*, 215(6), (Dec. 1968), 1488-1492.

Sigurdsson, A., et al., "The Role of Neurohormonal Activation in Chronic Heart Failure and Postmyocardial Infarction", *American Heart Journal*, 132(1, Part 2), (Jul. 1996), 229-234.

Takahashi, N., et al., "Vagal modulation of ventricular tachyarrhythmias induced by left ansae subclaviae stimulation in rabbits", *Japanese Heart Journal*, 39(4), (Jul. 1998), 503-511.

Thompson, G. W., "Bradycardia induced by intravascular versus direct stimulation of the vagus nerve", *Annals of Thoracic Surgery*, 65(3), (Mar. 1998), 637-642.

Tse, H. F., et al., "Long-term effect of right ventricular pacing on myocardial perfusion and function", *J Am Coll Cardiol.*, 29(4), (Mar. 15, 1997), 744-749.

Vanoli, E., et al., "Vagal Stimulation and Prevention of Sudden Death in Conscious Dogs With a Healed Myocardial Infarction", *Circulation Research*, 68(5), (May 1991), 1471-1481.

Veerman, D. P., et al., "Circadian profile of systemic hemodynamics", *Hypertension*, 26(1), (Jul. 1995), 55-59.

Verity, M. A., et al., "Plurivesicular nerve endings in the pulmonary artery", *Nature*, 211(48), (Jul. 30, 1966), 537-538.

Verity, M., et al., "Pulmonary artery innervation: a morphopharmacologic correlation", *Proceedings of the Western Pharmacology Society*, 8, (1965), 57-59.

Wallick, D. W., et al., "Selective AV nodal vagal stimulation improves hemodynamics during acute atrial fibrillation in dogs", *American Journal of Physiology—Heart & Circulatory Physiology*, 281(4), (Oct. 2001), H1490-H1497.

Waninger, M. S., et al., "Electrophysiological control of ventricular rate during atrial fibrillation", *Pacing & Clinical Electrophysiology*, 23(8), (Aug. 2000), 1239-44.

(56) References Cited

OTHER PUBLICATIONS

Wiggers, C J, et al., "The muscular reactions of the mammalian ventricles to artificial surface stimuli", *American Journal of Physiology*, (1925), 346-378.

Zamotrinsky, A. V., et al., "Vagal neurostimulation in patients with coronary artery disease", *Autonomic Neuroscience-Basic & Clinical*, 88(1-2), (Apr. 12, 2001), 109-116.

Zhang, Y., et al., "Optimal ventricular rate slowing during atrial fibrillation by feedback AV nodal-selective vagal stimulation", *American Journal of Physiology—Heart & Circulatory Physiology*, 282(3), (Mar. 2002), H1102-H1110.

Zhou, X., et al., "Prevention of high incidence of neurally mediated ventricular arrhythmias by afferent nerve stimulation in dogs", *Circulation*, 101(7), (Feb. 22, 2000), 819-824.

\* cited by examiner

MULTI-SITE VENTRICULAR PACING THERAPY WITH PARASYMPATHETIC STIMULATION

CROSS REFERENCE TO RELATED APPLICATION

This application is a continuation of U.S. application Ser. No. 10/700,368, filed Nov. 3, 2003, now issued as U.S. Pat. No. 7,657,312, which is hereby incorporated by reference in its entirety.

FIELD OF THE INVENTION

This patent application pertains to methods and apparatus for the treatment of cardiac disease. In particular, it relates to methods and apparatus for improving cardiac function with electro-stimulatory therapy.

BACKGROUND

Implantable cardiac devices that provide electrical stimulation to selected chambers of the heart have been developed in order to treat a number of cardiac disorders. A pacemaker, for example, is a device which paces the heart with timed pacing pulses, most commonly for the treatment of bradycardia where the ventricular rate is too slow. Atrio-ventricular conduction defects (i.e., AV block) and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate. Implantable devices may also be used to treat cardiac rhythms that are too fast, with either anti-tachycardia pacing or the delivery of electrical shocks to terminate atrial or ventricular fibrillation.

Implantable devices have also been developed that affect the manner and degree to which the heart chambers contract during a cardiac cycle in order to promote the efficient pumping of blood. The heart pumps more effectively when the chambers contract in a coordinated manner, a result normally provided by the specialized conduction pathways in both the atria and the ventricles that enable the rapid conduction of excitation (i.e., depolarization) throughout the myocardium. These pathways conduct excitatory impulses from the sino-atrial node to the atrial myocardium, to the atrio-ventricular node, and thence to the ventricular myocardium to result in a coordinated contraction of both atria and both ventricles. This both synchronizes the contractions of the muscle fibers of each chamber and synchronizes the contraction of each atrium or ventricle with the contralateral atrium or ventricle. Without the synchronization afforded by the normally functioning specialized conduction pathways, the heart's pumping efficiency is greatly diminished. Pathology of these conduction pathways and other inter-ventricular or intra-ventricular conduction deficits can be a causative factor in heart failure, which refers to a clinical syndrome in which an abnormality of cardiac function causes cardiac output to fall below a level adequate to meet the metabolic demand of peripheral tissues. In order to treat these problems, implantable cardiac devices have been developed that provide appropriately timed electrical stimulation to one or more heart chambers in an attempt to improve the coordination of atrial and/or ventricular contractions, termed cardiac resynchronization therapy (CRT). Ventricular resynchronization is useful in treating heart failure because, although not directly inotropic, resynchronization can result in a more coordinated contraction of the ventricles with improved pumping efficiency and increased cardiac output. Currently, a most common form of CRT applies stimulation pulses to both ventricles, either simultaneously or separated by a specified biventricular offset interval, and after a specified atrio-ventricular delay interval with respect to the detection an intrinsic atrial contraction.

One physiological compensatory mechanism that acts to increase cardiac output in heart failure patients is due to so-called backward failure which increases the diastolic filling pressure of the ventricles and thereby increases the preload (i.e., the degree to which the ventricles are stretched by the volume of blood in the ventricles at the end of diastole). An increase in preload causes an increase in stroke volume during systole, a phenomena known as the Frank-Starling principle. Thus, heart failure can be at least partially compensated by this mechanism but at the expense of possible pulmonary and/or systemic congestion. When the ventricles are stretched due to the increased preload over a period of time, however, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium which leads to alterations in cellular structure, a process referred to as ventricular remodeling. Hypertrophy can increase systolic pressures but also decreases the compliance of the ventricles and hence increases diastolic filling pressure to result in even more congestion. It also has been shown that the sustained stresses causing hypertrophy may induce apoptosis (i.e., programmed cell death) of cardiac muscle cells and eventual wall thinning which causes further deterioration in cardiac function. Thus, although ventricular dilation and hypertrophy may at first be compensatory and increase cardiac output, the processes ultimately result in both systolic and diastolic dysfunction. It has been shown that the extent of ventricular remodeling is positively correlated with increased mortality in CHF patients. It is with reversing such ventricular remodeling that the present invention is primarily concerned.

SUMMARY

The present invention relates to a method and device for delivering multi-site ventricular pacing therapy in conjunction with stimulation of parasympathetic nerves innervating the heart. Such parasympathetic stimulation acts to decrease the stresses experienced by the ventricular walls during systole so as to prevent or reverse the cardiac remodeling which can occur in heart failure patients. The parasympathetic stimulation may be delivered by an implantable cardiac device via a bipolar electrode incorporated into a lead adapted for transvenous insertion, such as into the superior or inferior vena cava. In order to counteract a tendency of parasympathetic stimulation to reduce cardiac output, the delivery of parasympathetic stimulation may be modulated in accordance with the patient's exertion level and/or a sensed parameter related to cardiac output.

DETAILED DESCRIPTION

One example of cardiac function therapy which may be delivered by an implantable cardiac device is CRT. In ventricular resynchronization therapy, the ventricles are paced at more than one site in order to cause a spread of excitation that results in a more coordinated contraction and thereby overcome interventricular or intraventricular conduction defects. Biventricular pacing is one example of resynchronization therapy in which both ventricles are paced in order to synchronize their respective contractions. Resynchronization therapy may also involve multi-site pacing applied to only one chamber. For example, a ventricle may be paced at multiple sites with excitatory stimulation pulses in order to produce multiple waves of depolarization that emanate from the pacing sites. This may produce a more coordinated contraction of the ventricle and thereby compensate for intraventricular conduction defects that may exist.

Another type of cardiac function therapy is stress reduction pacing. Stress reduction pacing uses multi-site pacing in order to change the distribution of wall stress experienced by the ventricle during the cardiac pumping cycle. The degree to which a heart muscle fiber is stretched before it contracts is termed the preload. The maximum tension and velocity of shortening of a muscle fiber increases with increasing preload. When a myocardial region contracts late relative to other regions, the contraction of those opposing regions stretches the later contracting region and increases the preload. The degree of tension or stress on a heart muscle fiber as it contracts is termed the afterload. Because pressure within the ventricles rises rapidly from a diastolic to a systolic value as blood is pumped out into the aorta and pulmonary arteries, the part of the ventricle that first contracts due to an excitatory stimulation pulse does so against a lower afterload than does a part of the ventricle contracting later. Thus a myocardial region which contracts later than other regions is subjected to both an increased preload and afterload. This situation is created frequently by the ventricular conduction delays associated with heart failure and ventricular dysfunction. The heart's initial physiological response to the uneven stress resulting from an increased preload and afterload is compensatory hypertrophy in those later contracting regions of the myocardium. In the later stages of remodeling, the regions may undergo atrophic changes with wall thinning due to the increased stress, and the extent of remodeling is positively correlated with mortality in heart failure patients. The parts of the myocardium which contract earlier in the cycle, on the other hand, are subjected to less stress and are less likely to undergo hypertrophic remodeling. This phenomenon may be used to cause reversal of remodeling by pacing one or more sites in a ventricle (or an atrium) with one or more excitatory stimulation pulses during a cardiac cycle with a specified pulse output sequence. The pace or paces are delivered in a manner that excites a previously stressed and remodeled region of the myocardium earlier during systole so that it experiences less afterload and preload. The pre-excitation of the remodeled region relative to other regions unloads the region from mechanical stress and allows reversal of remodeling to occur.

Heart failure patients may thus benefit from multi-site ventricular pacing for the purpose of improving cardiac output with more coordinated contractions and/or for the purpose of reducing ventricular wall stresses. A further decrease in ventricular wall stress may be obtained by, in conjunction with multi-site ventricular pacing, electrically stimulating parasympathetic nerves which innervate the heart. Sympathetic and parasympathetic nerves act on the heart via beta-adrenergic and muscarinic receptors, respectively, to affect both heart rate and myocardial contractility. A predominance of sympathetic over parasympathetic stimulation of the heart, for example, increases both intrinsic heart rate (via receptors at the sino-atrial node) and the strength of ventricular contractions. Stimulation of cardiac parasympathetic nerves, on the other hand, decreases myocardial contractility and hence reduces ventricular wall stresses. When delivered in conjunction with multi-site ventricular pacing for the treatment of heart failure, such parasympathetic stimulation can thus be beneficial in reversing or preventing cardiac remodeling.

Parasympathetic stimulation may be delivered by an implantable cardiac device via a bipolar electrode incorporated into a lead adapted for transvenous insertion, such as into the superior or inferior vena cava. In another embodiment, the bipolar electrode may be incorporated within a shock lead normally used for delivering cardioversion/defibrillation shocks to the heart. A pulse generator in the device then delivers electrical stimulation via the bipolar electrode to the inner surface of the blood vessel and stimulates the parasympathetic nerves that run adjacent thereto. Alternative sites for stimulating parasympathetic nerves also exist such as the atrial fat pad and others well-known to those of skill in the art. The electrical stimulation may be, for example, in the form of a square-wave or truncated exponential pulse train at a frequency of between 5 and 50 Hz. The result of such electrical stimulation is a slowing of sinus rhythm due to increased parasympathetic activity acting on the sino-atrial node as well as a negative inotropic effect which decreases ventricular wall stresses during systole.

Parasympathetic stimulation causes both a slowing of the intrinsic heart rate and a decrease in myocardial contractility, both of which tend to decrease cardiac output. Such a result may be undesirable in a heart failure patient, the beneficial effects on remodeling notwithstanding. An implantable device for delivering the parasympathetic stimulation in conjunction with multi-site ventricular pacing therapy, however, may counteract this undesirable result by several means, any or all of which may be employed. Firstly, if the multi-site ventricular pacing therapy is delivered in accordance with a demand pacing mode which enforces a minimum heart rate, no slowing of the heart rate occurs. Secondly, the decrease in cardiac output which would otherwise be brought about by a decrease in cardiac output may be compensated for by improved coordination of ventricular contractions due to the multi-site pacing. Thirdly, the device may be programmed to modulate the delivery of parasympathetic stimulation in accordance with a sensed parameter which reflects the patient's demand for cardiac output and/or the patient's actual cardiac output. In one embodiment, the device measures the patient's exertion level with a minute ventilation sensor or an accelerometer and delivers parasympathetic stimulation only when the measured exertion level is below a specified limit value. Alternatively, the extent of parasympathetic stimulation may be made to vary inversely with the measured exertion level. In another embodiment, the device measures the patient's cardiac output and delivers parasympathetic stimulation either in proportion to the measured cardiac output or only when the cardiac output exceeds a specified limit value. In another embodiment, measurements of cardiac output and exertion level are combined to compute a parameter which indicates the adequacy of the measured cardiac output. For example, a look-up table may be used to match a particular exertion level with a minimum cardiac output considered to be adequate. The device may then be programmed to deliver parasympathetic stimulation only if cardiac output is at a level considered to be adequate to meet metabolic demand.

What follows is a description of an exemplary implantable cardiac device which may be used to practice the invention as described above. An exemplary algorithm by which the device may implement parasympathetic stimulation is also described.

1. Exemplary Device Description

An implantable cardiac device is typically placed subcutaneously or submuscularly in a patient's chest with leads threaded intravenously into the heart to connect the device to electrodes used for sensing and stimulation. Leads may also be positioned on the epicardium by various means. A programmable electronic controller causes the stimulus pulses to be output in response to lapsed time intervals and sensed electrical activity (i.e., intrinsic heart beats not as a result of a stimulus pulse). The device senses intrinsic cardiac electrical activity by means of internal electrodes disposed near the chamber to be sensed. A depolarization wave associated with an intrinsic contraction of the atria or ventricles that is detected by the device is referred to as an atrial sense or ventricular sense, respectively. In order to cause such a contraction in the absence of an intrinsic beat, a stimulus pulse (a.k.a. a pace or pacing pulse when delivered in order to enforce a certain rhythm) with energy above a certain threshold is delivered to the chamber.

Figure 1:
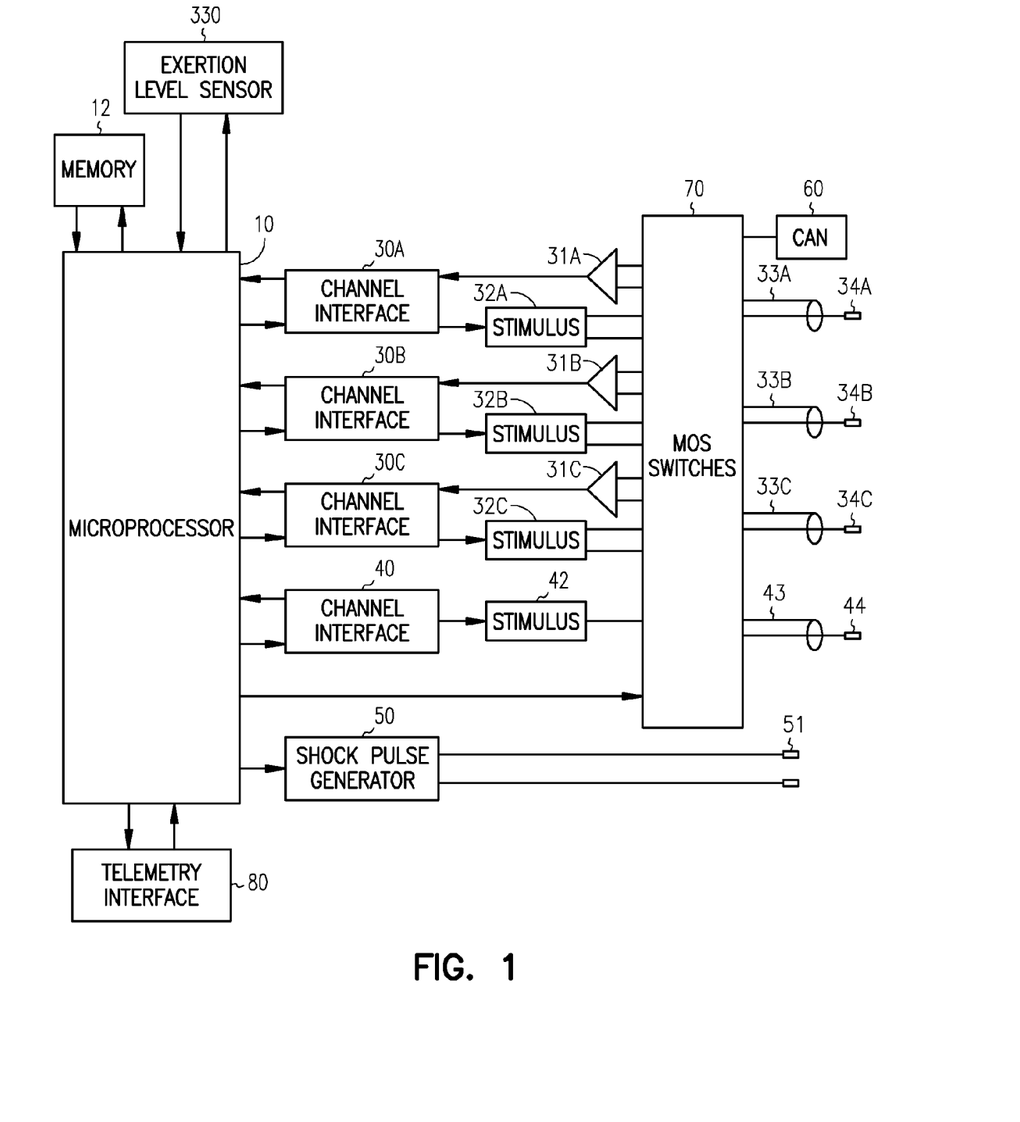
FIG. 1 is a system diagram of a cardiac device configured for multi-site stimulation and sensing.

FIG. 1 shows a system diagram of a microprocessor-based cardiac device suitable for practicing the present invention. The device is equipped with multiple sensing and pacing channels which may be physically configured to sense and/or pace multiple sites in the atria or the ventricles. The device shown in FIG. 1 can be configured for cardiac resynchronization pacing of the atria or ventricles and/or for myocardial stress reduction pacing such that one or more cardiac sites are sensed and/or paced in a manner that pre-excites at least one region of the myocardium. The multiple sensing/pacing channels may be configured, for example, with one atrial and two ventricular sensing/stimulation channels for delivering biventricular resynchronization therapy, with the atrial sensing/pacing channel used to deliver biventricular resynchronization therapy in an atrial tracking mode as well as to pace the atria if required. The controller 10 of the device is a microprocessor which communicates with a memory 12 via a bidirectional data bus. The memory 12 typically comprises a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. As used herein, the term "circuitry" should be taken to refer to either discrete logic circuitry or to the programming of a microprocessor.

Shown in the figure are three exemplary sensing and pacing channels designated "a" through "c" comprising bipolar leads with ring electrodes 34a-c and tip electrodes 33a-c, sensing amplifiers 31a-c, pulse generators 32a-c, and channel interfaces 30a-c. Each channel thus includes a pacing channel made up of the pulse generator connected to the electrode and a sensing channel made up of the sense amplifier connected to the electrode. The channel interfaces 30a-c communicate bidirectionally with microprocessor 10, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing, and the intrinsic atrial and/or ventricular rates can be detected by measuring the time intervals between atrial and ventricular senses, respectively. A stimulation channel is also provided for delivering parasympathetic stimulation which includes a bipolar lead with a ring electrode 44 and a tip electrode 43, a pulse generator 42, and a channel interfaces 40.

The electrodes of each bipolar lead are connected via conductors within the lead to a MOS switching network 70 controlled by the microprocessor. The switching network is used to switch the electrodes to the input of a sense amplifier in order to detect intrinsic cardiac activity and to the output of a pulse generator in order to deliver a pacing pulse. The switching network also enables the device to sense or pace either in a bipolar mode using both the ring and tip electrodes of a lead or in a unipolar mode using only one of the electrodes of the lead with the device housing or can 60 serving as a ground electrode. A shock pulse generator 50 is also interfaced to the controller for delivering a defibrillation shock via a pair of shock electrodes 51 to the atria or ventricles upon detection of a shockable tachyarrhythmia.

The controller 10 controls the overall operation of the device in accordance with programmed instructions stored in memory, including controlling the delivery of paces via the pacing channels, interpreting sense signals received from the sensing channels, and implementing timers for defining escape intervals and sensory refractory periods. An exertion level sensor 330 (e.g., an accelerometer, a minute ventilation sensor, or other sensor that measures a parameter related to metabolic demand) enables the controller to adapt the pacing rate in accordance with changes in the patient's physical activity and, as described above, enables the controller to modulate the delivery of parasympathetic stimulation. A telemetry interface 80 is also provided which enables the controller to communicate with an external programmer.

In one embodiment, the exertion level sensor is a minute ventilation sensor which includes an exciter and an impedance measuring circuit. The exciter supplies excitation current of a specified amplitude (e.g., as a pulse waveform with constant amplitude) to excitation electrodes that are disposed in the thorax. Voltage sense electrodes are disposed in a selected region of the thorax so that the potential difference between the electrodes while excitation current is supplied is representative of the transthoracic impedance between the voltage sense electrodes. The conductive housing or can may be used as one of the voltage sense electrodes. The impedance measuring circuitry processes the voltage sense signal from the voltage sense electrodes to derive the impedance signal. Further processing of the impedance signal allows the derivation of signal representing respiratory activity and/or cardiac blood volume, depending upon the location the voltage sense electrodes in the thorax. (See, e.g., U.S. Pat. Nos. 5,190, 035 and 6,161,042, assigned to the assignee of the present invention and hereby incorporated by reference.) If the impedance signal is filtered to remove the respiratory component, the result is a signal that is representative of blood volume in the heart at any point in time, thus allowing the computation of stroke volume and, when combined with heart rate, computation of cardiac output. The stroke volume integrated over time (or averaged and multiplied by heart rate) gives the patient's cardiac output. A look-up table or other function may be used to compute what cardiac output is considered adequate for a given exertion level. As described above, a measurement of cardiac output or a determination of the adequacy of the cardiac output may be used by the device to modulate the delivery of parasympathetic stimulation.

The controller is capable of operating the device in a number of programmed pacing modes which define how pulses are output in response to sensed events and expiration of time intervals. Most pacemakers for treating bradycardia are programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity such that a pacing pulse is delivered to a heart chamber during a cardiac cycle only after expiration of a defined escape interval during which no intrinsic beat by the chamber is detected. Escape intervals for ventricular pacing can be restarted by ventricular or atrial events, the latter allowing the pacing to track intrinsic atrial beats. Cardiac function therapy, whether for the purpose of cardiac resynchronization or for reversal of remodeling, is most conveniently delivered in conjunction with a bradycardia pacing mode where, for example, multiple excitatory stimulation pulses are delivered to multiple sites during a cardiac cycle in order to both pace the heart in accordance with a bradycardia mode and provide pre-excitation of selected sites.

A particular pacing mode for delivering cardiac function therapy, whether for stress reduction or resynchronization, includes a defined pulse output configuration and pulse output sequence, where the pulse output configuration specifies a specific subset of the available electrodes to be used for delivering pacing pulses and the pulse output sequence specifies the timing relations between the pulses. The pulse output configuration is defined by the controller selecting particular pacing channels for use in outputting pacing pulses and by selecting particular electrodes for use by the channel with switch matrix 70. The pulse output configuration and sequence which optimally effects reverse remodeling by selectively reducing myocardial wall stress may or may not be the optimum pulse output configuration and sequence for maximizing hemodynamic performance by resynchronizing ventricular contractions. For example, a more hemodynamically effective contraction may be obtained by exciting all areas of the myocardium simultaneously, which may not effectively promote reversal of the hypertrophy or remodeling. In that instance, however, delivery of parasympathetic stimulation in conjunction with the multi-site pacing may reduce ventricular wall stresses while still maintaining adequate cardiac output.

b. Exemplary Algorithm

An exemplary algorithm is described below which could be applied in the case of a heart failure patient whose cardiac output is inadequate because of a conduction deficit and who is at risk for ventricular remodeling. Simply providing parasympathetic stimulation to reduce ventricular wall stress would lessen the risk of remodeling but could also further decrease the patient's already inadequate cardiac output. By combining parasympathetic stimulation with multi-site ventricular resynchronization pacing (e.g., biventricular pacing), however, the patient's ventricular function can improved so as to allow the parasympathetic stimulation without adversely affecting cardiac output. In order to further insure that the patient's cardiac output remains adequate, measurements of cardiac output and exertion level can be made by the implantable device with the adequacy of the cardiac output then determined from an appropriate mapping function. Delivery of parasympathetic stimulation can then be delivered or not based upon this determination.

Figure 2:
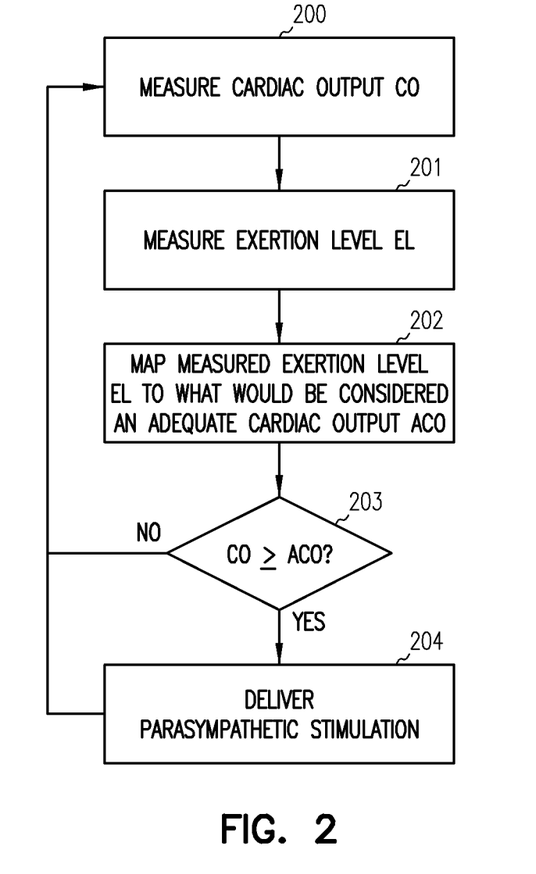
FIG. 2 illustrates an exemplary algorithm for implementing the invention.

FIG. 2 illustrates an exemplary algorithm for delivering parasympathetic stimulation in conjunction with multi-site ventricular pacing as could be implemented by appropriate programming of the implantable device controller. The algorithm is performed concurrently with the delivery of ventricular resynchronization pacing therapy. Starting at step 200, the device measures cardiac output CO by the impedance technique described above. At step 201, the patient's exertion level EL is measured by measuring either minute ventilation or body acceleration. The device then maps the measured exertion level EL to a cardiac output ACO which would be considered adequate for that exertion level at step 202. At step 203, the measured cardiac output CO is compared with the computed adequate cardiac output ACO. If the measured cardiac output is adequate (i.e., if CO≥ACO plus a possible safety margin), parasympathetic stimulation is delivered at step 204.

Although the invention has been described in conjunction with the foregoing specific embodiments, many alternatives, variations, and modifications will be apparent to those of ordinary skill in the art. Such alternatives, variations, and modifications are intended to fall within the scope of the following appended claims.

What is claimed is:

1. An implantable device for delivering cardiac function therapy to a patient, comprising:

pulse generation circuitry for delivering pacing pulses to multiple ventricular sites and for delivering stimulation pulses to parasympathetic nerves innervating the heart;

a controller configured for controlling the delivery of pacing pulses to the multiple ventricular sites and the delivery of the parasympathetic stimulation;

a sensor configured for measuring cardiac output;

an exertion level sensor configured for measuring the patient's exertion level;

wherein the controller is programmed to deliver the multi-site ventricular pacing therapy while the parasympathetic stimulation is being delivered and wherein the controller is further programmed to deliver the multi-site ventricular pacing therapy with a pacing pulse output sequence that pre-excites at least one myocardial region relative to other regions for reducing ventricular wall stress; and, wherein the controller is further programmed to deliver the multi-site ventricular pacing in a manner that enforces a minimum ventricular rate;

wherein the controller is programmed to compute a function that maps exertion levels to minimum cardiac output values considered to be adequate for a particular exertion level and is further programmed to cease the delivery of parasympathetic stimulation if the current measurement of the exertion level maps to a minimum cardiac output value that is greater than the current measurement of cardiac output.

2. The device of claim 1 wherein the cardiac output sensor is a trans-thoracic impedance measuring circuit.

3. The device of claim 1 wherein the controller is programmed to deliver the parasympathetic stimulation only when cardiac output is above a specified limit value.

4. The device of claim 1 wherein the controller is programmed to modulate the delivery of parasympathetic stimulation in accordance with the measured exertion level.

5. The device of claim 1 wherein the controller is programmed to deliver the parasympathetic stimulation only when the measured exertion level is below a specified limit value.

6. The device of claim 1 wherein the controller is programmed to compute the function that maps exertion levels to minimum cardiac output values considered to be adequate for a particular exertion level using a look-up table.

7. The device of claim 1 wherein the exertion level sensor is a minute ventilation sensor.

8. The device of claim 1 wherein the exertion level sensor is an accelerometer.

9. An implantable device for delivering cardiac function therapy to a patient, comprising:
- means for delivering pacing pulses to multiple ventricular sites and for delivering stimulation pulses to parasympathetic nerves innervating the heart;
- means for measuring cardiac output;
- means for measuring the patient's exertion level;
- means for delivering the multi-site ventricular pacing therapy while the parasympathetic stimulation is being delivered and to deliver the multi-site ventricular pacing therapy with a pacing pulse output sequence that pre-excites at least one myocardial region relative to other regions for reducing ventricular wall stress; and,
- means for delivering the multi-site ventricular pacing in a manner that enforces a minimum ventricular rate;
- means for computing a function that maps exertion levels to minimum cardiac output values considered to be adequate for a particular exertion level and means for ceasing the delivery of parasympathetic stimulation if the current measurement of the exertion level maps to a minimum cardiac output value that is greater than the current measurement of cardiac output.

* * * * *